(12) United States Patent
Laermer et al.

(10) Patent No.: US 10,295,441 B2
(45) Date of Patent: May 21, 2019

(54) METHOD AND DEVICE FOR PRODUCING A MICROFLUIDIC ANALYSIS CARTRIDGE

(71) Applicant: Robert Bosch GmbH, Stuttgart (DE)

(72) Inventors: Franz Laermer, Weil Der Stadt (DE); Juergen Steigert, Stuttgart (DE); Sven Zinober, Friolzheim (DE)

(73) Assignee: Robert Bosch GmbH, Stuttgart (DE)

( * ) Notice: Subject to any disclaimer, the term of this patent is extended or adjusted under 35 U.S.C. 154(b) by 865 days.

(21) Appl. No.: 14/254,968

(22) Filed: Apr. 17, 2014

(65) Prior Publication Data

US 2014/0322100 A1    Oct. 30, 2014

(30) Foreign Application Priority Data

Apr. 26, 2013 (DE) .................. 10 2013 207 683

(51) Int. Cl.
*G01N 1/28* (2006.01)
*B01L 3/00* (2006.01)
(Continued)

(52) U.S. Cl.
CPC ............ *G01N 1/28* (2013.01); *B01L 3/50273* (2013.01); *B01L 3/502707* (2013.01);
(Continued)

(58) Field of Classification Search
CPC ..... B01L 2300/0867; B01L 2300/0887; B01L 2200/027; F04B 43/02; G01N 27/44791;
(Continued)

(56) References Cited

U.S. PATENT DOCUMENTS 6,293,012 B1 *  9/2001  Moles ............... B01L 3/502707
                                                29/890.124
2006/0076068 A1    4/2006  Young et al.
(Continued)

FOREIGN PATENT DOCUMENTS

CN       102319956 A        1/2012
DE   102009051514 A1  *   5/2011
(Continued)

OTHER PUBLICATIONS

EPO machine translation of "Specification" for DE 102009051514 A1 (Busch et al.); published May 5, 2011.*

*Primary Examiner* — Lyle Alexander
*Assistant Examiner* — Bryan Kilpatrick
(74) *Attorney, Agent, or Firm* — Maginot, Moore & Beck LLP

(57) ABSTRACT

A method for producing a pneumatically actuatable microfluidic analysis cartridge includes closing a joining side of a fluidic part of the analysis cartridge with a first fluid-tight elastic membrane and/or closing a joining side of a pneumatic part of the analysis cartridge with a second membrane. The fluidic part is configured to perform fluidic basic operations of a biochemical analysis process, and the pneumatic part is configured to control the basic operations using air pressure. The joining side of the fluidic part and the joining side of the pneumatic part are aligned, and the fluidic part and the pneumatic part are connected to form the analysis cartridge.

21 Claims, 10 Drawing Sheets

(51) Int. Cl.
*F16K 99/00* (2006.01)
*B81C 3/00* (2006.01)
*B29C 65/16* (2006.01)
*B29C 65/00* (2006.01)
*B65B 3/00* (2006.01)
*B29L 31/00* (2006.01)

(52) U.S. Cl.
CPC .......... *B01L 3/502715* (2013.01); *B65B 3/00* (2013.01); *B81C 3/001* (2013.01); *B81C 3/005* (2013.01); *F16K 99/0015* (2013.01); *F16K 99/0026* (2013.01); *F16K 99/0055* (2013.01); *B01L 2200/02* (2013.01); *B01L 2200/025* (2013.01); *B01L 2200/0689* (2013.01); *B01L 2300/0816* (2013.01); *B01L 2300/0887* (2013.01); *B01L 2300/123* (2013.01); *B01L 2400/0487* (2013.01); *B01L 2400/0655* (2013.01); *B29C 65/1612* (2013.01); *B29C 65/1616* (2013.01); *B29C 65/1635* (2013.01); *B29C 66/112* (2013.01); *B29C 66/114* (2013.01); *B29C 66/1122* (2013.01); *B29C 66/53461* (2013.01); *B29C 66/71* (2013.01); *B29C 66/7392* (2013.01); *B29C 66/929* (2013.01); *B29L 2031/756* (2013.01); *B81B 2201/058* (2013.01); *B81C 2203/035* (2013.01); *B81C 2203/036* (2013.01); *B81C 2203/054* (2013.01)

(58) Field of Classification Search
CPC .............. G01N 30/6095; B01J 19/0093; B01J 2219/00783
USPC .................... 422/129, 505; 436/178; 53/410
See application file for complete search history.

(56) References Cited

U.S. PATENT DOCUMENTS

| | | | |
|---|---|---|---|
| 2007/0084706 A1* | 4/2007 | Takayama et al. | ........... 200/182 |
| 2007/0137779 A1* | 6/2007 | Mori | ........... B29C 65/1635 |
| | | | 156/272.8 |
| 2010/0167384 A1 | 7/2010 | Clemmens et al. | |
| 2011/0086433 A1* | 4/2011 | Rupp | ........... 436/180 |
| 2011/0241226 A1* | 10/2011 | Reinecke et al. | ........... 257/787 |

FOREIGN PATENT DOCUMENTS

| | | |
|---|---|---|
| EP | 1 520 621 A2 | 4/2005 |
| EP | 2 032 255 B1 | 3/2009 |
| EP | 2 138 233 A1 | 12/2009 |
| EP | 2 322 277 A1 | 5/2011 |
| WO | 2011/042422 A1 | 4/2011 |

* cited by examiner

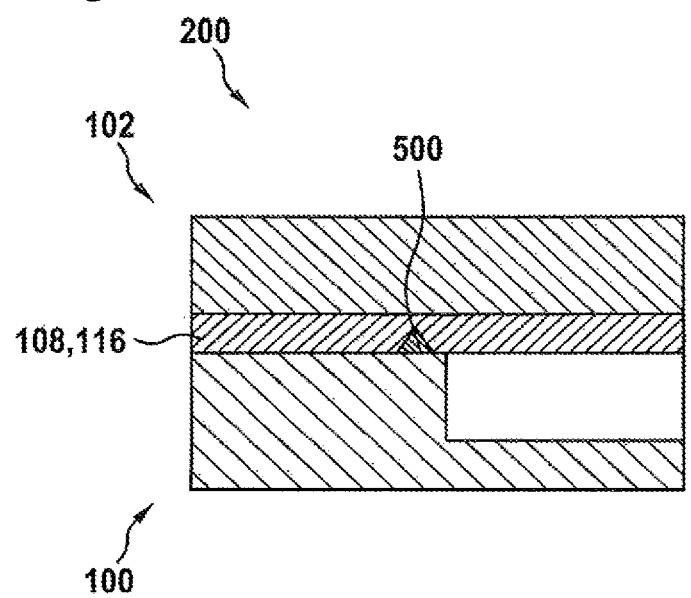
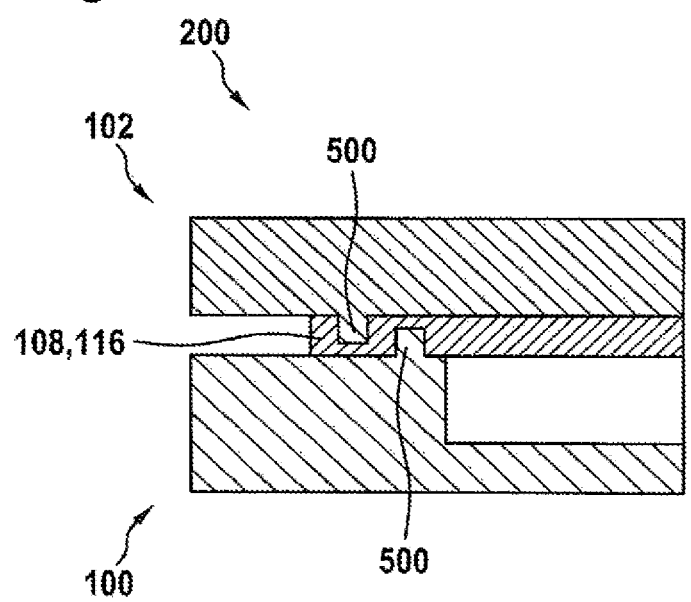

METHOD AND DEVICE FOR PRODUCING A MICROFLUIDIC ANALYSIS CARTRIDGE

This application claims priority under 35 U.S.C. § 119 to patent application no. DE 10 2013 207 683.5, filed on Apr. 26, 2013 in Germany, the disclosure of which is incorporated herein by reference in its entirety.

The present disclosure relates to a method for producing a pneumatically actuatable microfluidic analysis cartridge, to a corresponding device, and to a corresponding computer program product.

BACKGROUND

An analysis cartridge can be designed to perform at least one biochemical process in a disposable unit. For this purpose, the analysis cartridge is charged with a sample and placed in an analysis appliance. The process is controlled and evaluated in the analysis appliance. At the end of the process, the cartridge is removed from the analysis appliance and disposed of.

WO 2011/042422 A1 describes a joining method and joint for microfluidic components.

SUMMARY

Against this background, the present disclosure proposes a method for producing a pneumatically actuatable microfluidic analysis cartridge, a device for producing a pneumatically actuatable microfluidic analysis cartridge, and, finally, a corresponding computer program product. Advantageous embodiments are set forth in claims and in the description below.

An analysis cartridge for an analysis process has at least two functionally different layers, which are arranged adjacent to each other in a predefined position relative to each other. The analysis process is performed in a first layer. The first layer is closed in a fluid-tight manner, in order to store fluids of the analysis process and receive reaction products. In a second layer, movements and forces are made available for performing the analysis process in the first layer. To make available the movements and forces, chambers that are likewise closed in a fluid-tight manner are needed so as to be able to build up pressure or underpressure therein.

In order to obtain fluid-tight sealing of a cartridge, the cartridge can be sealed with a membrane. Each of the layers can be sealed separately, in order to achieve optimal leak-tightness. The layers can then be joined together to form the cartridge.

A method for producing a pneumatically actuatable microfluidic analysis cartridge is proposed, which method has the following steps:
provision of a fluidic part of the analysis cartridge and of a pneumatic part of the analysis cartridge, wherein the fluidic part is designed to perform fluidic basic operations of a biochemical analysis process, and the pneumatic part is designed to control the basic operations using air pressure;
closure of a joining side of the fluidic part with a first fluid-tight elastic membrane and/or closure of a joining side of the pneumatic part with a second membrane;
alignment of the joining side of the fluidic part with respect to the joining side of the pneumatic part; and
connection of the fluidic part and of the pneumatic part, in order to obtain the analysis cartridge.

Thus, at least one membrane can be used, which is joined to a substrate. If only a single membrane is used, both the joining side of the fluidic part and also the joining side of the pneumatic part can be closed by this one membrane. If two membranes are used, then, in the step of alignment, the first membrane can be aligned on the second membrane.

A pneumatically actuatable analysis cartridge can be understood as a unit for use in an analysis appliance, which unit is equipped with reagents necessary for at least one chemical and/or biochemical analysis process and is designed to perform the one or more corresponding analysis processes in corresponding devices when the analysis appliance provides energy in the form of pressure. A fluidic part can have ducts, chambers and structures for performing the analysis process. A pneumatic part can have chambers, ducts and structures for controlling the analysis process using overpressure and/or underpressure. The first membrane and the second membrane can complement an effect of each other. The first membrane and the second membrane can safely separate the fluidic part and the pneumatic part from each other. An alignment can be a determinate mounting. For example, the alignment can be the fixing of a first point in three axes, of a second point in two of the three axes, and of a third point in one of the three axes. For example, the membranes can lie flat on each other, as a result of which the membranes are fixed in a plane transverse to the membranes. The first and second points can be prevented from a movement in a first main direction of the plane of the membranes, while the first point is also prevented from a movement in a second main direction of the plane. A connection can be a force-fit connection, a form-fit connection and/or a cohesive connection.

The first membrane and the fluidic part and, alternatively or in addition, the second membrane and the pneumatic part can be connected using laser energy. The laser energy can be directed onto the joining side. The laser energy can melt at least one material at an interface between the membrane and the part, such that a cohesive connection is achieved. Laser energy can be easily directed.

The first membrane and the second membrane can be connected to each other cohesively over at least a partial surface area. The cohesive connection allows tensile forces to be transmitted via both membranes.

The fluidic part and the pneumatic part can be pressed onto each other mechanically. Good sealing can be achieved by means of the force-fit connection.

The first membrane and, alternatively or in addition, the second membrane can be coated over at least a partial surface area, in order to modify diffusion properties and, alternatively or in addition, permeation properties of the membrane. A coating can be applied after the closure.

Thus, for example, closure can be carried out with the laser without restriction prior to the coating, and the coating can be applied independently of a closure contour. The coating is well protected after the connection between the membranes.

A third elastic membrane can be arranged between the first membrane and the second membrane. By means of a third membrane, the membranes can be selectively strengthened, for example in order to be able to better transmit forces from the pneumatic part to the fluidic part.

The fluidic part and, alternatively or in addition, the pneumatic part can be provided with a means of sealing which protrudes from the joining face, wherein the means of sealing can be pressed into the first membrane and, alternatively or in addition, into the second membrane, in order to connect the fluidic part and the pneumatic part in a fluid-tight manner. A means of sealing can be a circumferentially closed sealing lip. The means of sealing can improve a secure closure of the fluidic part and/or of the pneumatic part.

The fluidic part and the pneumatic part can be provided with at least two guide elements and, in the step of alignment, the fluidic part and the pneumatic part can be aligned on each other using the guide elements. The guide elements can be used to align the first point and the second point. With planar contact of the membranes, two guide elements can ensure a statically determinate mounting.

The first membrane can be aligned on the guide elements of the fluidic part or of the pneumatic part. Alternatively or in addition, the second membrane can be aligned on the guide elements of the pneumatic part or of the fluidic part. The membranes can be aligned on the guide elements prior to the closure. In this way, the membranes can be positioned reliably and quickly.

The fluidic part and, alternatively or in addition, the pneumatic part can be pressurized, in order to connect the first membrane to the second membrane. By means of the pressure, surface pressing between the membranes can be achieved and the connection improved.

Furthermore, a device for producing a pneumatically actuatable microfluidic analysis cartridge is proposed, which device has the following features:
a means for provision of a fluidic part of the analysis cartridge and of a pneumatic part of the analysis cartridge, wherein the fluidic part is designed to perform fluidic basic operations of a biochemical analysis process, and the pneumatic part is designed to control the basic operations using air pressure;
a means for closure of a joining side of the fluidic part with a first fluid-tight elastic membrane and/or closure of a joining side of the pneumatic part with a second membrane;
a means for alignment of the joining side of the fluidic part with respect to the joining side of the pneumatic part; and
a means for connection of the fluidic part and of the pneumatic part, in order to obtain the analysis cartridge.

A device can be understood here as an electrical apparatus that processes sensor signals and, as a function thereof, outputs control and/or data signals. The device can have an interface that can be configured as hardware and/or software. In a hardware configuration, the interfaces can, for example, be part of what is called an ASIC system, which contains a wide variety of functions of the device. However, it is also possible that the interfaces are dedicated, integrated circuits or are composed at least in part of discrete structural elements. In a software configuration, the interfaces can be software modules which, for example, are present on a microcontroller in addition to other software modules.

A computer program product with a program code which can be stored on a machine-readable carrier such as a semiconductor memory, a hard-disk memory or an optical memory, and is used to carry out the method according to one of the above-described embodiments when the program product is executed on a computer or a device, is also advantageous.

A pneumatically actuatable microfluidic analysis cartridge has the following features:
a fluidic part, which is designed to perform fluidic basic operations of a biochemical analysis process;
a pneumatic part, which is designed to control the basic operations using compressed air; and
at least one fluid-tight elastic membrane for closure of a joining side of the fluidic part and/or for closure of a joining side of the pneumatic part, wherein the at least one fluid-tight elastic membrane is arranged between the fluidic part and the pneumatic part.

According to one embodiment, the pneumatically actuatable microfluidic analysis cartridge can have a first elastic membrane for closure of the joining side of the fluidic part, and a second elastic membrane for closure of the joining side of the pneumatic part. The first membrane and the second membrane can be arranged between the fluidic part and the pneumatic part. Advantageously, the first membrane and the second membrane can differ from each other in that they are transparent for laser light of different wavelengths. In this way, the laser welding of the fluidic part can be carried out using laser light of a first wavelength for which the first membrane is transparent, and the laser welding of the pneumatic part can be carried out using laser light of a second wavelength for which the second membrane is transparent.

The joining side of the fluidic part and the joining side of the pneumatic part can be made from different materials. For example, the whole fluidic part and the whole pneumatic part can be produced from different materials. The different materials can have different material properties which, for example, are unsuitable for a direct join between the different materials, for example by laser welding. However, using the at least one membrane, such a fluidic part and such a pneumatic part can be reliably joined together.

BRIEF DESCRIPTION OF THE DRAWINGS

The disclosure is explained in more detail below by way of example and with reference to the attached drawings, in which:

FIG. 5 shows a view of a fluidic part with a means for sealing an analysis cartridge according to an illustrative embodiment of the present disclosure;

FIG. 6 shows a view of a fluidic part and of a pneumatic part, each with a means for sealing an analysis cartridge according to an illustrative embodiment of the present disclosure;

In the following description of expedient illustrative embodiments of the present disclosure, identical or similar reference signs are used for the elements that are shown in the various figures and that have a similar effect, the aim being to avoid repeated description of these elements.

DETAILED DESCRIPTION

The performance of biochemical processes is based on the manipulation of liquids. Typically, this manipulation can be performed manually using aids such as pipets, reaction vessels, active probe surfaces or laboratory equipment. These processes can be partially automated with pipetting robots or specialized equipment.

A lab-on-a-chip (LOC) system (also called a pocket laboratory or chip laboratory) is a microfluidic system that accommodates the entire functionality of a macroscopic laboratory on a plastic substrate of, for example, only the size of a plastic card. Lab-on-a-chip systems are typically composed of two main components. The first main component is a test carrier or a disposable cartridge that contains structures and mechanisms for the fluidic basic operations (e.g. mixing), which can consist of passive components such as ducts, reaction chambers, pre-stored reagents, or also active components such as valves or pumps. The second main component involves actuation units, detection units and control units. The system permits fully automated processing of biochemical processes.

Figure 1:
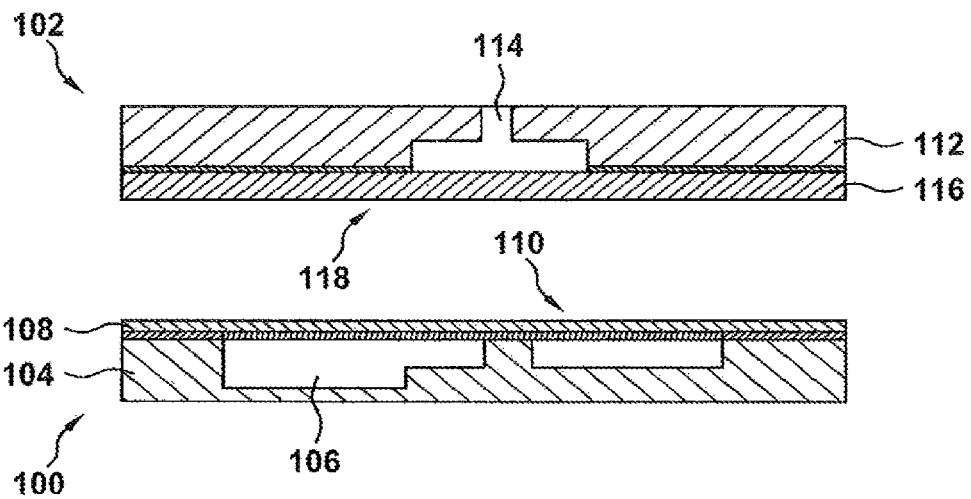
FIG. 1 shows a view of a fluidic part and of a pneumatic part of an analysis cartridge according to an illustrative embodiment of the present disclosure.

FIG. 1 shows a view of a fluidic part 100 and of a pneumatic part 102 of an analysis cartridge according to an illustrative embodiment of the present disclosure. The fluidic part 100 has a first substrate 104, a first structure 106 and a first membrane 108. The first structure 106 is closed in a fluid-tight manner by the first membrane 108 on a joining face 110 of the fluidic part 100. The pneumatic part 102 has a second substrate 112, a second structure 114 and a second membrane 116. The second structure 114 is closed by the second membrane 116 on a joining face 118 of the pneumatic part 102. The joining faces 110, 118 are aligned facing each other. In the view of the illustrative embodiment shown in FIG. 1, the fluidic part 100 is arranged at the bottom and the pneumatic part 102 at the top. The first substrate 104 is designed as absorber for absorbing laser radiation. The first membrane 108 is made from a material transparent to the laser radiation. In this way, upon closure of the fluidic part 100, the laser radiation is able to pass through the first membrane 108 in order to heat the first substrate 104 at least at the surface, until the first substrate 104 melts on a surface (laser weld surface) irradiated by the laser radiation, so as to connect in a fluid-tight manner to the first membrane 108. The second substrate 112 is made from a material transparent to the laser radiation. The second membrane 116 is designed as absorber for absorbing the laser radiation. In this way, upon closure of the pneumatic part 102, the laser radiation is able to pass through the second substrate 112 in order to heat the second membrane 116 at least at the surface, until the second membrane 116 melts on the surface irradiated by the laser radiation, so as to connect in a fluid-tight manner to the second substrate 112.

Figure 2:
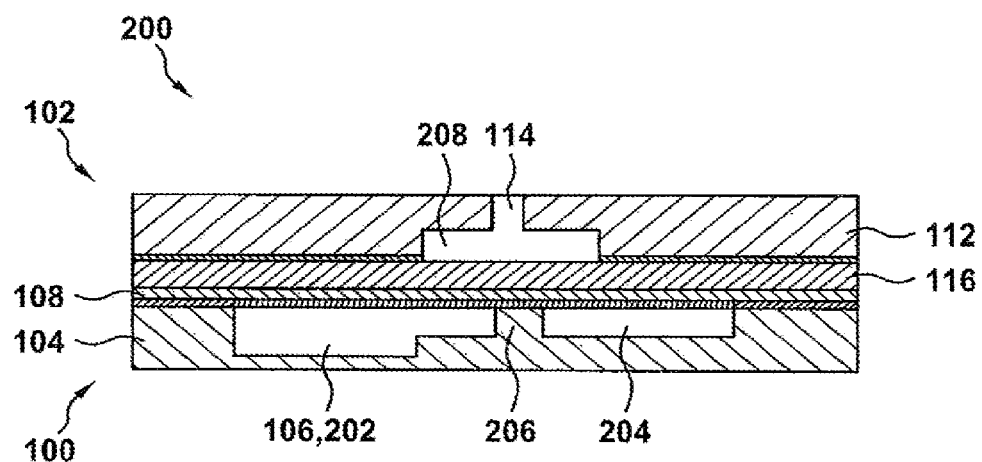
FIG. 2 shows a view of an analysis cartridge according to an illustrative embodiment of the present disclosure.

FIG. 2 shows a view of an analysis cartridge 200 according to an illustrative embodiment of the present disclosure. The analysis cartridge 200 has a fluidic part 100 and a pneumatic part 102, as shown in FIG. 1. The first membrane 108 is aligned with the second membrane 116, and the fluidic part 100 is connected to the pneumatic part 102. The first membrane 108 is arranged directly adjacent to the second membrane 116. According to this illustrative embodiment, the first membrane 108 is thinner than the second membrane 116. Alternatively, both membranes 108, 116 can be of the same thickness, or the first membrane 108 can be thicker than the second membrane 116. The first structure 106 has a first chamber 202 and a second chamber 204. The first chamber 202 is separated from the second chamber 204 by a web 206. The web bears on the first membrane 108 and separates the two chambers 202, 204 from each other in a fluid-tight manner, when the membrane 108 is in a starting position. The second structure 114 has a third chamber 208. The third chamber 208 is connected by an air duct to a rear face of the pneumatic part 102. When air is drawn off from the third chamber 208 via the air duct, the first membrane 108 and the second membrane 116 are pulled into the third chamber 208. In this way, a gap arises between the web 206 and the first membrane 108. The first chamber 202 is connected to the second chamber 204 via the gap. By way of the gap, liquid can be exchanged between the chambers 202, 204 in order to perform an analysis process in the fluidic part 100. The membranes 108, 116 and the web 206 thus act as a valve for controlling an exchange of liquid between the first chamber 202 and the second chamber 204.

FIGS. 1 and 2 show a longitudinal cross section of a structure 200. Ducts 106, 114 are located in the substrates 104, 112. These ducts 106, 114 are each sealed off by a membrane 108, 116, respectively. The substrate 104, 112 or the elastic membrane 108, 116 can be designed as absorber. Depending on the required properties, the two substrates 104, 112 or membranes 108, 116 can be made from different materials. The materials of substrate 104, 112 and membrane 108, 116 are advantageously designed for the respective process of laser-welding to each other. Any desired joining methods can be used for joining the two 2-layer stacks 100, 102.

The illustrative embodiment of a lab-on-chip system 200 shown here is designed as a pneumatic platform. A cartridge 200 in accordance with the approach proposed here is typically composed of at least 3 layers, there being at least one elastic membrane 108, 116 located between two rigid layers 104, 112 in which the fluidic and pneumatic structures 106, 114 are integrated. The multi-layer structure can be obtained by means of laser welding. Here, at least two of the layers are pressed together with a force F<2.5 kN. One of the layers serves as absorber and absorbs the energy of the irradiated laser radiation. In this way, the two layer materials are melted at their interface and the polymer chains are able to connect mechanically. Upon cooling, this state is "frozen", and a mechanical bond arises. Thus, two substrate layers are connected to each other via one joining layer and sealed off.

The active control of fluids on lab-on-chip cartridges 200 requires valves, which are integrated in the fluidic network 106. By applying an overpressure in the pneumatic structures 114, the elastic membranes 116, 108 can be deflected and press the fluidic duct 106 off, wherein the flow of fluid comes to a standstill. With this principle, further fluidic unit operators such as pumps, mixers or reaction chambers can be realized.

By means of the 4-layer structure proposed here, based on "thermoplastic/thermoplastic elastomer (TPE)/thermoplastic elastomer (TPE)/thermoplastic", robust LOC cartridges 200 can be constructed. The material combinations can be adapted precisely to one another in laser welding, a mechanical connection of the polymer chains can be optimized, and a robust bond results. The TPE middle layer 108, 116 can be designed as absorber. For joining by means of laser welding, the laser beam can thus be beamed directly onto the absorber 108, 116. An advantage of the laser welding here is that two layers are joined only selectively at defined locations. Since the substrates 104, 112 are structured, the laser beam would be deflected on chambers, ducts or webs if it were to act through the substrate 104, 112, as a result of which it is difficult to produce a continuous and fluidically tight weld contour of the fluidic network. Two of the layers are connected to each other and sealed off via one joining layer. This widens the possible material combinations, since the laser welding capability can be easily ensured.

Surface properties of the materials, in particular of the elastic membranes 108, 116, are critical for the fluidic network 106, since biological constituents in the liquid, such as proteins, enzymes, DNA strands, nucleotides or antibodies, may bind non-specifically to the surfaces and could thus be "fished out" of the solution and would no longer be available for the rest of the test. Other important parameters of the materials used are the permeation and diffusion behavior, particularly for water, water vapor, ethanol and oxygen.

The surface properties can be improved by a surface modification at the interface of elastic membrane 108, 116 and substrate 104, 112, i.e. at the joining face.

With the approach proposed here, it is possible to produce microfluidic lab-on-chip cartridges 200 from homogeneous and also from heterogeneous material combinations. The cartridge 200 typically consists of at least two substrates 104, 112, a pneumatic layer (layer 1) 102 and a fluidic layer (layer 2) 100, between which two elastomeric membranes (layer 3) 108, 116 are located. In the pneumatic layer 102, and also the fluidic layer 100, there are fluidic networks 106, 114, which typically consist of ducts, chambers and/or through-holes. The ducts typically have diameters of less than 1 mm and duct widths and depths of 1-3,000 μm. The integrated chambers can typically hold a volume of greater than 1 μl and up to 5 ml. The through-holes have diameters of 50 μm to 3 mm. The pneumatic layer 102 and fluidic layer 100 typically have a thickness of 1-10 mm. The elastic membranes 108, 116 typically have a thickness of 10-500 μm. The cartridges 200 are designed to realize fluidic unit operations, for example by valves, pumps, mixers and/or aliquoting structures.

In one embodiment, the fluidic layer 104 and the pneumatic layer 112 are each welded to an elastic membrane 108, 116. Thus, for example, the elastic membrane 108, 116 is not secured as absorber. Depending on the stack, the substrate 104, 112 or the elastic membrane 108, 116 can be designed as absorber. If the substrate 104, 112 is designed as absorber, an energy input can take place through the elastic membrane 108, 116, such that the laser beam is not deflected by duct walls or chambers of the kind present in the substrate 104, 112. Here, the substrate 104, 112 represents the absorber, and the membrane 108, 116 is transparent to the irradiated wavelength. Thus, when the laser beam passes through the membrane 108, 116, no refraction effects and scattering effects take place, as a result of which continuous and therefore fluidically tight weld contours can be generated around the fluidic network 106.

Since in each case only the substrate 104, 112 and the associated membrane 108, 116 are adapted to each other in respect of the joining by means of a laser welding process, different materials can be used for the membranes 108, 116 and substrates 104, 112. The joining of the 2-layer stacks 100, 102 can then be carried out by any joining methods, e.g. adhesive bonding or surface pressure.

As substrates for the fluidic layer 104, thermoplastics are typically used, such as COP, COC, PC, PA, PU, PP, PET or PMMA. Alternatively, structured glasses or metals can also be used. In one illustrative embodiment, the mechanical pressing is done under vacuum in order to avoid the inclusion of air bubbles between fluidic layer 104 and elastic membrane 108. Alternatively or in addition, it is also possible for the pneumatic network 114 and/or the fluidic network 106 to be pressurized, which may prove particularly advantageous in the design with two membranes that are adhesively connected, in order to achieve good binding particularly in the valve area.

The elastic membrane 108, 116 does not necessarily have to be joined at the top or bottom to the pneumatic or fluidic layer 104, 112 or to a further elastic membrane. In one illustrative embodiment, the joining takes place selectively only with one of the layers.

In one embodiment, heterogeneous materials are used for the different substrate layers, e.g. COC and PC. In one embodiment, the substrate materials are adapted to each other such that the coefficient of thermal expansion is almost identical for the range of −30 to +100° C. (e.g. PC 70* $10^{-6}$/K and COP 60*$10^{-6}$/K) or a maximum of 20% different.

Furthermore, in the design of multi-layer systems, the individual layers can be designed and combined variably and flexibly as absorbers or transparent to wavelengths of the laser welding. In one illustrative embodiment, the pneumatic layer 112 is designed as absorber and the associated elastic membrane 116 is transparent, while the fluidic layer 104 is transparent, wherein pneumatic and fluidic layers 104, 112 are each joined with an elastic membrane 108, 116, and the elastic membrane 108 assigned to the fluidic layer 104 is designed to be absorbing.

In one embodiment, the pneumatic network 114 is also completely or partially filled segmentally with a liquid, as a result of which a hydraulic actuation takes place.

Figure 3:
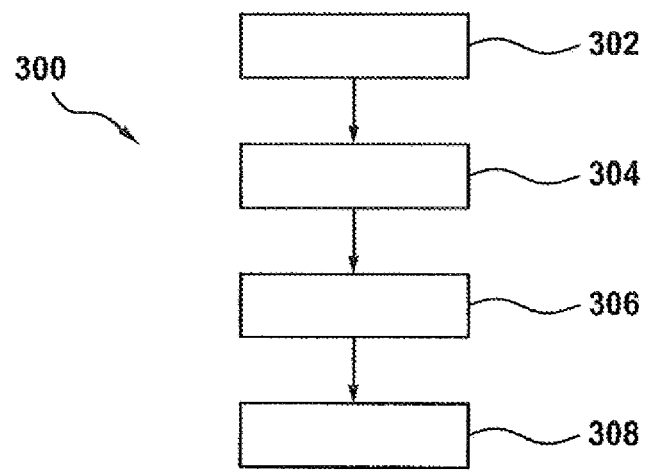
FIG. 3 shows a flow diagram of a method for producing an analysis cartridge according to an illustrative embodiment of the present disclosure.

FIG. 3 shows a flow diagram of a method 300 for producing a pneumatically actuatable microfluidic analysis cartridge according to an illustrative embodiment of the present disclosure. The method 300 has a step 302 of provision, a step 304 of closure, a step 306 of alignment, and a step 308 of connection. In the step 302 of provision, a fluidic part of the analysis cartridge and a pneumatic part of the analysis cartridge are provided, wherein the fluidic part is designed to perform fluidic basic operations of a biochemical analysis process, and the pneumatic part is designed to control the basic operations using air pressure. In the step 304 of closure, a joining side of the fluidic part is closed with a first fluid-tight elastic membrane. Furthermore, a joining side of the pneumatic part is closed with a second membrane. In the step 306 of alignment, the first membrane and the second membrane are aligned on each other. In the step 308 of connection, the fluidic part and the pneumatic part are connected to each other, in order to obtain the analysis cartridge.

In one illustrative embodiment, in the step 304 of closure, the first membrane and the fluidic part and, alternatively or in addition, the second membrane and the pneumatic part are connected using laser energy, wherein the laser energy is directed onto the joining side. The laser energy is directed in the form of directional laser light through the membrane onto the substrate arranged beneath. Material of the membrane and/or material of the substrate is plasticized in the area of an interface between the substrate and the membrane. When the plasticized material cools, the membrane connects cohesively to the substrate.

In one illustrative embodiment, in the step 308 of connection, the first membrane and the second membrane are connected to each other cohesively over at least a partial surface area. For example, the membranes can be bonded to each other using an adhesive layer.

In one illustrative embodiment, in the step 308 of connection, the fluidic part and the pneumatic part are pressed onto each other mechanically. Joining forces between the substrate of the fluidic part and the substrate of the pneumatic part can be built up that press both parts onto each other.

In one illustrative embodiment, in the step 304 of closure, the first membrane and, alternatively or in addition, the second membrane are coated over at least a partial surface area, in order to modify diffusion properties and, alternatively or in addition, permeation properties of the membrane. For example, at least one of the membranes can be coated with metal in order to obtain an effective diffusion barrier.

In one illustrative embodiment, in the step 306 of alignment, a third elastic membrane is arranged between the first membrane and the second membrane. The third membrane can be designed as a stiffening for the first membrane and/or the second membrane. The third membrane can be adhesively bonded to at least one of the membranes. The third membrane can, for example, concentrate a pressure force from the pneumatic part onto a small effective surface area.

In one illustrative embodiment, in the step 302 of provision, the fluidic part and, alternatively or in addition, the pneumatic part is provided with a means of sealing which protrudes from the joining face, wherein the means of sealing is pressed, in the step of connection, into the first membrane and, alternatively or in addition, the second membrane, in order to connect the fluidic part and the pneumatic part in a fluid-tight manner. The means of sealing can compress the membranes more strongly in order to achieve improved sealing.

In one illustrative embodiment, in the step 302 of provision, the fluidic part and the pneumatic part are provided with at least two guide elements. In the step 306 of alignment, the fluidic part and the pneumatic part are aligned on each other using the guide elements. Guide elements can have contact faces for aligning the parts to each other. The guide elements can also have centering aids, for example bevels or chamfers.

In one illustrative embodiment, in the step 304 of closure, the first membrane is aligned on the guide elements of the fluidic part. Alternatively or in addition, the second membrane is aligned on the guide elements of the pneumatic part. The membrane can be fitted onto the guide elements prior to the closure. For this purpose, the membrane has receiving openings corresponding with the guide elements.

In one illustrative embodiment, in the step 306 of connection, the fluidic part and/or the pneumatic part are pressurized, in order to connect the first membrane to the second membrane. By means of the pressure, the membranes can be connected to each other flat.

The approach proposed here describes a device and a method for the construction of pneumatic multi-layer lab-on-chip (LOC) cartridges with multiple elastomeric sealing films.

By the approach proposed here, fluidically leak-free joining of heterogeneous material combinations is possible with a pressure stability of greater than three bar. The joining method proposed here is independent of surface properties of the heterogeneous or homogeneous materials used. The joining method proposed here results in continuous and fluidically tight weld contours. The approach proposed here permits a modification of the diffusion and permeation properties of the layer materials before or after the construction of the cartridge. The approach proposed here permits a modification of the diffusion and permeation properties of the elastic membranes. The approach proposed here permits a modification of the surface properties of the layer materials in order to avoid non-specific binding of biologically relevant substances. The approach proposed here permits a flexible combination of heterogeneous materials.

Figure 4:
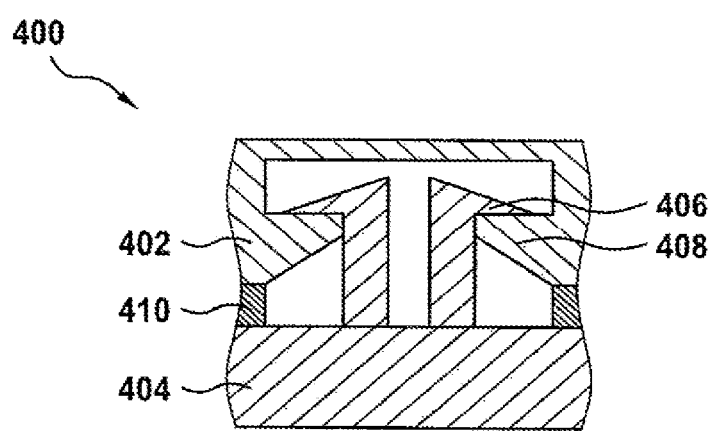
FIG. 4 shows a view of a guide element for connecting a fluidic part and a pneumatic part of an analysis cartridge according to an illustrative embodiment of the present disclosure.

FIG. 4 shows a view of a guide element 400 for connecting a first part 402 and a second part 404 of an analysis cartridge according to an illustrative embodiment of the present disclosure. First part 402 and second part 404 can represent both the fluidic part and also the pneumatic part as are shown in FIGS. 1 and 2. An example of a click mechanism 400 is shown for permanently connecting and maintaining a mechanical pressure between the fluidic part and the pneumatic part. Here, all the components of the click closure 400 can be produced directly in the production process of the basic substrates 402, 404. For example, as click finger 406 of the second layer 404 by injection molding. The click finger 406 is designed to latch in a retaining structure 408 of the first layer 402. The joining is then effected by pressing the fluidic layer with the pneumatic layer or the membrane stack 410. The click mechanism 400 can also have multiple retaining lugs 406 and retaining structures 408.

In a further embodiment, the pneumatic layer and the fluidic layer are held together via a ratchet, snap-fit or click mechanism 400.

FIG. 5 shows a view of a fluidic part 100 with a means 500 for sealing an analysis cartridge 200 according to an illustrative embodiment of the present disclosure. The means 500 for sealing is designed as a protruding structure from a contact face between the fluidic part 100 and the first membrane 108, as is shown in FIGS. 1 and 2. The means of sealing 500 can be designated as a sealing lip 500. The first membrane 108 and the second membrane 116 are arranged between the fluidic part 100 and the pneumatic part 102. The means 500 of sealing locally narrows a spacing between the fluidic part 100 and the pneumatic part 102. In this way, the first membrane 108 and the second membrane 116 are squeezed in the area of the sealing lip 500 and an increased sealing action is achieved.

In one illustrative embodiment, the sealing lip 500 is pressed into the membranes 108, 116 in order to improve sealing only at the time of a planned use of the analysis cartridge 200 in an analysis appliance, and this is done by a pressure exerted on the analysis cartridge 200 by the analysis appliance.

FIG. 6 shows a view of a fluidic part 100 and of a pneumatic part 102, each with a means 500 of sealing an analysis cartridge 200 according to an illustrative embodiment of the present disclosure. As in FIG. 5, the means 500 are designed as protruding structure. The means 500 are arranged laterally offset in relation to each other. The means can also be arranged lying opposite each other in order to increase the squeezing of the two membranes 108, 116.

For better sealing, a sealing lip 500 is integrated in the pneumatic layer 102 and/or fluidic layer 100 and additionally compresses the elastic membranes 108, 116. In FIG. 5, the sealing lip 500 is triangular. In FIG. 6, complementary sealing lips 500 are arranged offset in the pneumatic layer 102 and fluidic layer 100. In one illustrative embodiment, the elastic membranes 108, 116 are structured.

In one embodiment, the fluidic network is surrounded by sealing lips 500 which, during the joining operation, press into the elastic membrane 108, 116 and reinforce the sealing.

In a further embodiment, the pneumatic layer 112 and/or the fluidic layer 104 has a means 500 which comprises the fluidic structures 106 and acts as a sealing lip 500. The sealing lip 500 engages into the elastic membrane 108, 116 and compresses or displaces the latter and thus ensures an increased sealing. The sealing lip 500 typically has a height of less than 80% of the thickness of the elastic membrane 108, 116, typically between 10 µm and 100 µm height and width. Moreover, both fluidic layer and pneumatic layer 104, 112 can have complementary sealing lips 500 which face each other or are offset in relation to each other. In a further embodiment, the elastic membrane 108, 116 is, for example, folded as pneumatic and fluid layer 104, 112 around complementary and slightly offset sealing lips 500. The sealing lip 500 can have any desired cross-sectional geometries, e.g. rectangular, triangular or rounded.

Figure 7:
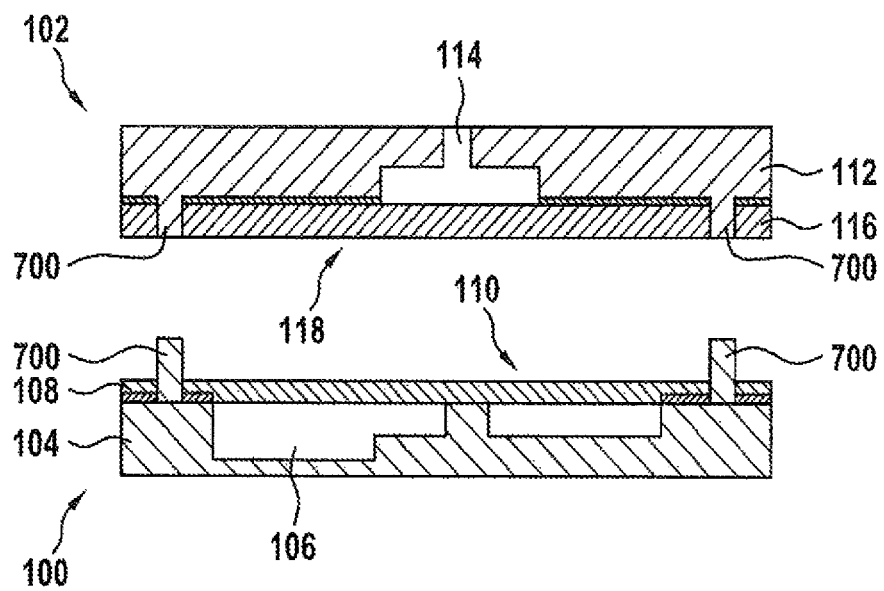
FIG. 7 shows a view of a fluidic part and of a pneumatic part with guide elements according to an illustrative embodiment of the present disclosure.

FIG. 7 shows a view of a fluidic part 100 and of a pneumatic part 102 with guide elements 700 according to an illustrative embodiment of the present disclosure. The fluidic part 100 and the pneumatic part 102 correspond to the view in FIGS. 1 and 2. In addition, the fluidic part 100 has two dowel pins 700 as guide elements. The dowel pins 700 protrude, perpendicular to the first joining face 110, from the first substrate 104 and the first membrane 108. The pneumatic part 102 has two bores 700 matching the dowel pins 700 and serving as guide elements. The bores 700 or recesses pass through the second membrane 116 and end as blind holes in the second substrate 112.

In one illustrative embodiment, the fluidic layer 104 is joined, analogously to the pneumatic layer 112, to an elastic membrane 108 by means of laser welding. Thereafter, the pneumatic layer stack 102 and the fluidic layer stack 100 are joined to each other by mechanical pressing, such that the two elastic membranes 108, 116 are in contact with each other. The stacks 100, 102 are aligned with each other before being joined or during the joining process, e.g. by integrated dowel pins 700. Various methods can be used for the joining operation. For example, mechanical pressing, adhesive bonds, click mechanisms, caulking, laminating (optionally with temperature) or laser welding.

Figure 8:
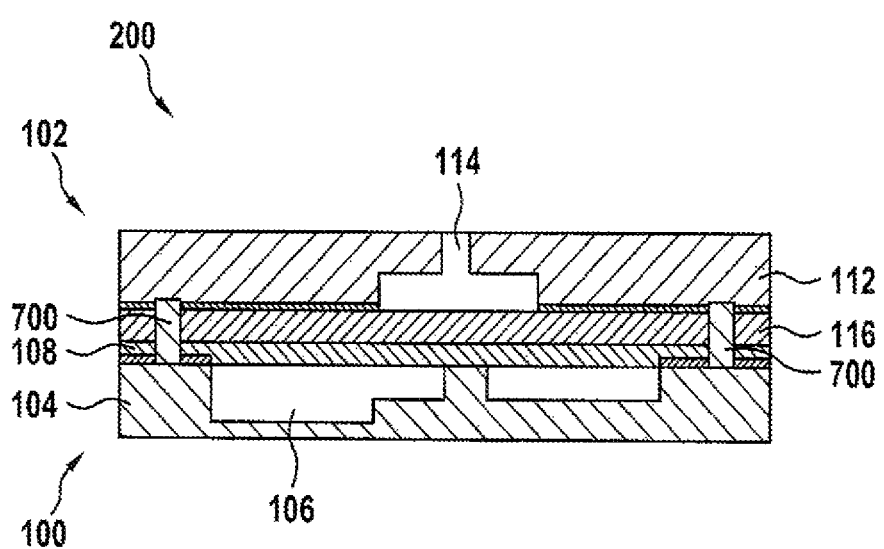
FIG. 8 shows a view of an analysis cartridge with guide elements according to an illustrative embodiment of the present disclosure.

FIG. 8 shows a view of an analysis cartridge 200 with guide elements 700 according to an illustrative embodiment of the present disclosure. The analysis cartridge 200 corresponds to the view in FIG. 2 and is composed of the fluidic part 100 and of the pneumatic part 102, with the membranes 108, 116 arranged between these. The dowel pins 700 are arranged in the blind holes 700 and define a position of the parts 100, 102 relative to each other.

In one illustrative embodiment, the LOC cartridge 200 is constructed from two stacks 100, 102. Each stack 100, 102 is composed of a substrate 104, 112 with fluidic structures 106, 114 and an elastic membrane 108, 116 joined by means of laser welding. Substrates 104, 112 and membranes 108, 116 can each be made from different materials. The alignment is effected by integrated dowel pins 700 in a substrate 104 and by corresponding bores 700 in the mating piece 112. The stacks 100, 102 are joined by mechanical pressing, such as an adhesive bond or dowel pins 700 with click mechanisms. In the illustrative embodiment shown, the fluidic part 100 and the pneumatic part 102 are connected by an adhesive join.

In one embodiment, different joining methods are combined. In particular, for the mechanical pressing, it is possible, for example, for joining pins 700 to be combined with ratchet mechanisms or multiple clamping or click structures. Likewise, two layers can be connected by adhesive joining, in which case joining pins 700 as dowel pins are used for a precise alignment, without reinforcing the adhesive join.

In one embodiment, the joining methods described here are used only to produce a mechanical connection and alignment of the components. The forces needed for the complete sealing of the cartridge are applied only when the cartridge 200 is placed in the evaluation unit (DxU). In this way, it is possible to effectively prevent possible relaxation of the join during long-term storage.

Figure 9:
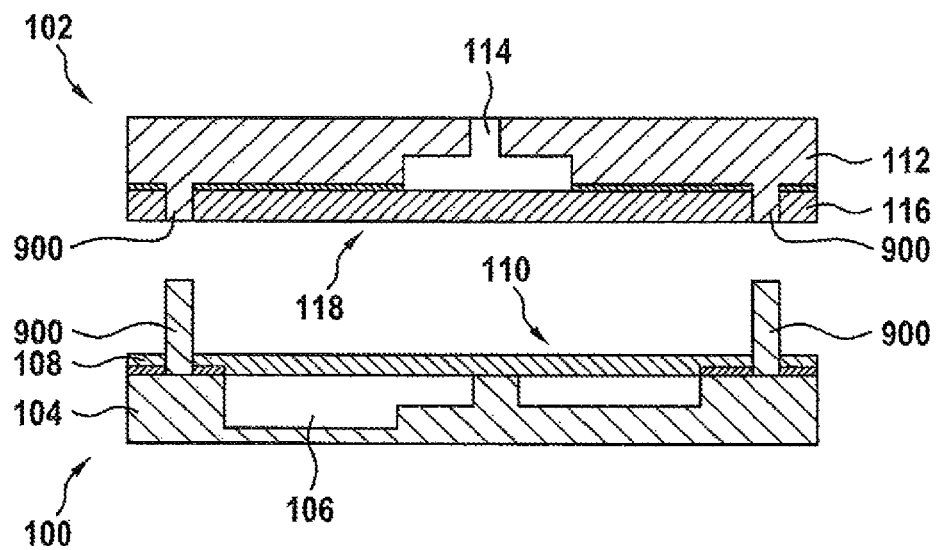
FIG. 9 shows a view of a fluidic part and of a pneumatic part with connection elements according to an illustrative embodiment of the present disclosure.

FIG. 9 shows a view of a fluidic part 100 and of a pneumatic part 102 with connection elements 900 according to an illustrative embodiment of the present disclosure. The fluidic part 100 and the pneumatic part 102 correspond to the illustrative embodiment shown in FIG. 7. In contrast to the latter, the guide elements are designed as connection elements 900. The connection elements 900 are designed on the fluidic part 100 as bolts, which are designed to perform a guiding function. The bolts 900 are longer than the dowel pins in FIG. 7. The connection elements 900 are designed in the pneumatic part 102 as through-holes extending from the joining face 118 to a rear face of the pneumatic part 102. The bolts 900 are so long that they reach through the through-holes 900 as far as the rear face and can be secured there. The bolts 900 and the through-holes 900 are designed matching each other.

Figure 10:
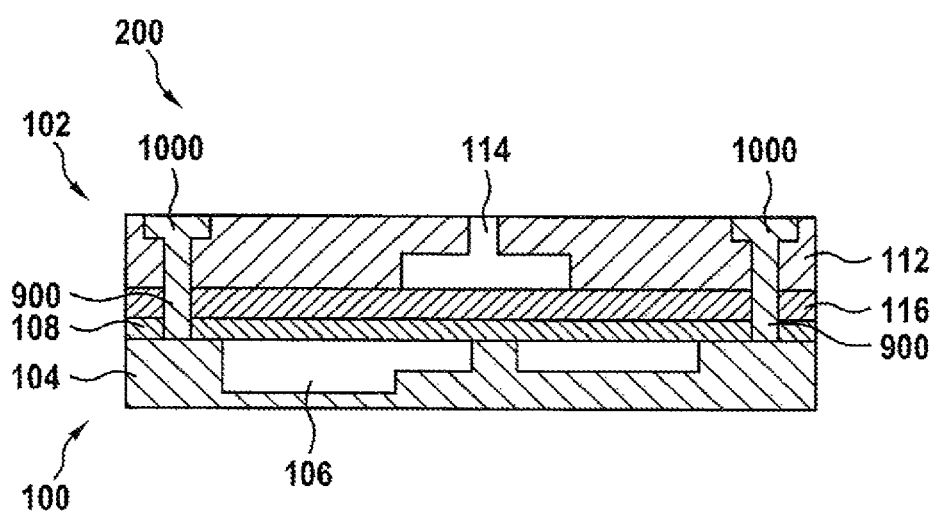
FIG. 10 shows a view of an analysis cartridge with connection elements according to an illustrative embodiment of the present disclosure.

FIG. 10 shows a view of an analysis cartridge 200 with connection elements 900 according to an illustrative embodiment of the present disclosure. The analysis cartridge 200 corresponds to the illustrative embodiment shown in FIG. 8. In contrast to the latter, the guide elements are designed as connection elements 900 as in FIG. 9. The bolts 900 are arranged in the through-holes 900 and each have, on the rear face of the pneumatic part 102, a thickening 1000 for form-fit connection. The thickenings 1000 have greater dimensions than the through-bores 900. The thickenings 1000 can be reshaped material of the bolts 900. The fluidic part 100 can then be riveted to the pneumatic part 102. Likewise, the bolts 900 can have threads, and the thickenings 1000 can be designed as nuts or screws.

In one illustrative embodiment, the LOC cartridge 200 is constructed from two stacks 100, 102. Each stack 100, 102 is composed of a substrate 104, 112 with fluidic structures 106, 114 and an elastic membrane 108, 116 joined by means of laser welding. Substrates 104, 112 and membranes 108, 116 can each be made from different materials. The alignment is effected by integrated dowel pins 900 in a substrate 104 and by corresponding recesses 900 in the mating piece 112. The stacks 100, 102 are joined by mechanical pressing, e.g. rivets 1000. The membranes 108, 116 are not connected to each other. This means that a first membrane 108 can transmit the deformation to the second membrane 116 only in the event of deflection by overpressure, not underpressure.

Figure 11:
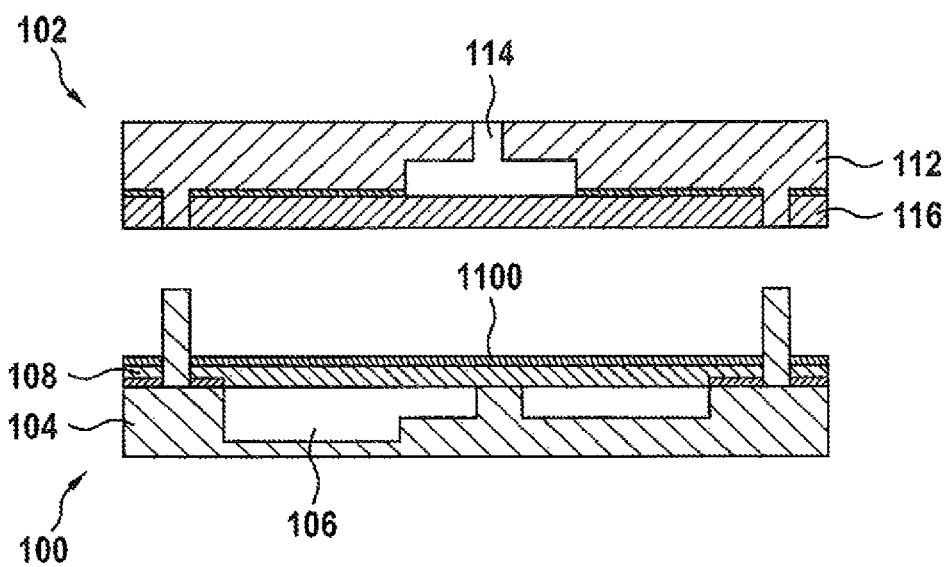
FIG. 11 shows a view of a fluidic part with coated membrane according to an illustrative embodiment of the present disclosure.

FIG. 11 shows a view of a fluidic part 100 with coated membrane 108 according to an illustrative embodiment of the present disclosure. A pneumatic part 102 is also shown. The fluidic part 100 and the pneumatic part 102 correspond to the view in FIGS. 9 and 10. In addition, the first membrane 108 is coated in order to modify diffusion properties and/or permeability properties of the first membrane 108.

Figure 12:
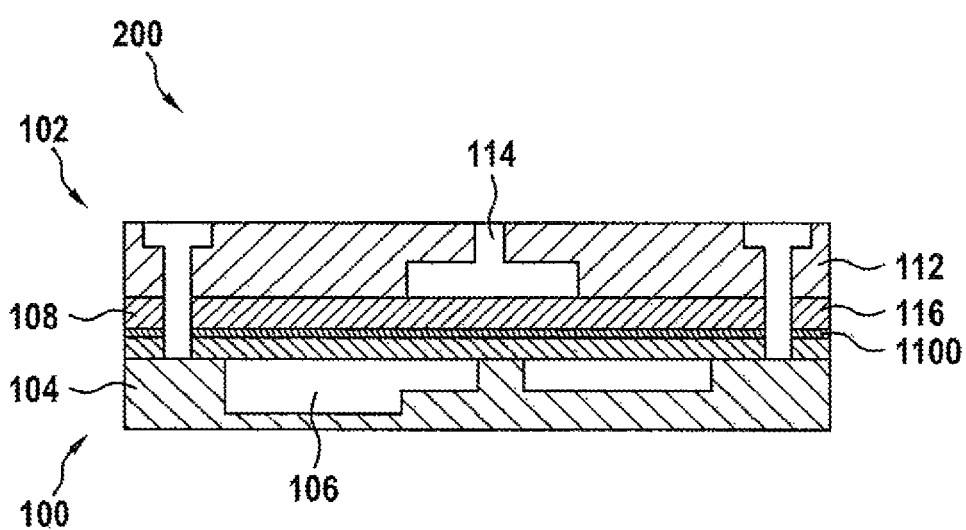
FIG. 12 shows a view of an analysis cartridge with coated membrane according to an illustrative embodiment of the present disclosure.

FIG. 12 shows a view of an analysis cartridge 200 with a coated membrane 108 according to an illustrative embodiment of the present disclosure. The analysis cartridge 200 corresponds to the analysis cartridge in FIG. 10. In addition, the first membrane 108 of the fluidic part 100 is coated as in FIG. 11.

The surface of the membrane 108, which is not laser-welded, is modified. For example, a metal layer 1100 is arranged as diffusion barrier on the membrane 108. This can also serve as a join between the two 2-layer stacks 100, 102 or be partially buried, in which case a further joining face is applied outside the coating 1100.

In one embodiment, the diffusion or permeation properties of the membrane 108, 116 are optimized. For this purpose, the surface of the elastic membrane 108, 116 of one stack 100, 102, which is later joined to the second stack 100, 102, is coated. Metallic layers such as aluminum, or fluorine-based layers such as Teflon, are particularly suitable. When the two two-layer stacks 100, 102 are joined, the applied layer is buried, for example as diffusion barrier, between the two membranes 108, 116. Thus, for example, gas diffusion from the fluidic layer 100 into the pneumatic layer 102 or into the environment can be suppressed. It is advantageous that the diffusion material, which is often not biocompatible, does not come into contact at all with the fluidic network.

In one illustrative embodiment, a further elastic material 1100 is introduced between the two stacks 100, 102. Different elastic membranes 1100 with different geometries (e.g. thicknesses, recesses, external dimensions, shapes) can be used for the stacks 100, 102.

In one embodiment, the surfaces of the elastic membrane 108, 116 and/or the surfaces of the fluidic layer 104, or at least of the fluidic structure 106 in the fluidic layer 104, are coated. The coating can, for example, avoid non-specific bindings of enzymes, DNA strands, RNA strands, nucleotides or proteins such as polymerases, ligases or antibodies. The coating can, for example, modify diffusion or permeation properties of the membrane 108, 116. Possible coatings are Parylene, PEG, hydrogels, fluorinations, in particular PTFE coating, silicon oxide or glass. The coating can be carried out flat or selectively structured before the joining operation. It is also possible to coat different areas with different materials. Physical modifications, such as plasma treatments or implantation of substances, can also be used. Moreover, the surface modification can also be carried out after the joining operation.

Moreover, the surface modification can serve to drastically reduce the diffusion and permeation of gases and liquids, such that the storage of liquids such as buffers (e.g. washing buffer, hybridization buffer, lysis buffer), ethanol solutions, PCR master mix with DNA solutions, RNA solutions, enzyme solutions, protein solutions, nucleotide solutions, is possible over a longer period of time (more than 6 months). Possible examples of coatings here are, for example, glass, silicone oxide or aluminum.

Figure 13:
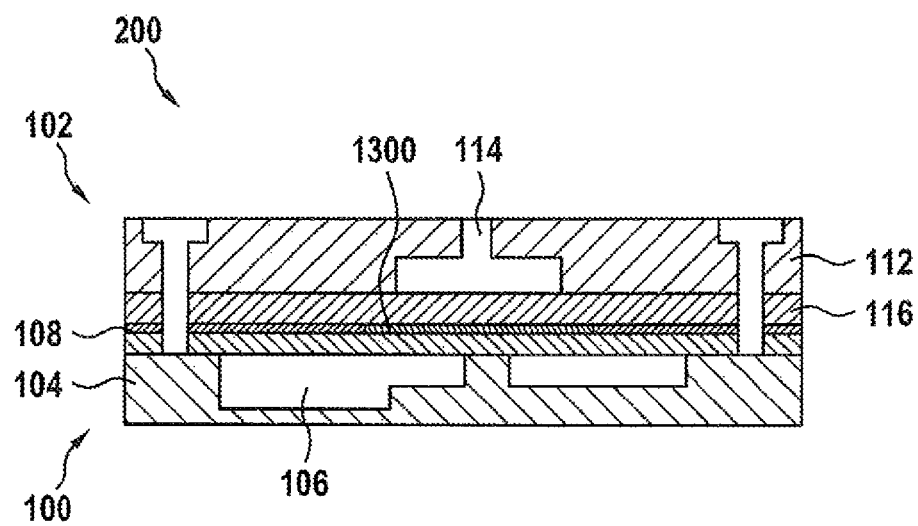
FIG. 13 shows a view of an analysis cartridge with partially coated membrane according to an illustrative embodiment of the present disclosure.

FIG. 13 shows a view of an analysis cartridge 200 with a partially coated membrane 108 according to an illustrative embodiment of the present disclosure. The analysis cartridge 200 corresponds to the analysis cartridge in FIG. 12. In contrast to the latter, the first membrane 108 of the fluidic part 100 is only partially coated. A remaining surface of the membrane 108 is uncoated.

In one embodiment, the membranes 108, 116 are joined by means of a selective adhesive bond 1300. The adhesive bond 1300 extends over defined partial surface areas of the membranes 108, 116. The fluidic part 100 and the pneumatic part are connected by joining pins 700 for pressing the two stacks 100, 102 together. The deflection of the membrane 116 of the pneumatic part 102 by application of an overpressure is transmitted directly to the membrane 108 of the fluid stack 100, as a result of which this membrane is also deflected. In this way, active fluidic elements can be produced, as with cartridges constructed purely by laser welding. If the elastic membranes 108, 116 are also intended to be suctioned, i.e. through actuation by application of a vacuum to the pneumatic stack 102, then both membranes 108, 116 can be fixedly connected to each other, e.g. by means of adhesive bonding, thermal joining or adhesive layers 1300. The fixed joining of the elastic membranes 108, 116 can be planar or structured or localized at defined positions or partial surface areas. In order to modify the diffusion or permeation properties of the membrane 108, 116, the surface of the elastic membrane 108, 112 of one stack 100, 102, which is later joined to the second stack 100, 102, can be coated.

On account of the compatibility of the membrane surface to the process of laser welding, a surface modification of the laser join surface 110, 118 is not possible. Since the membrane surface opposite the laser join surface 110, 118 is accessible in the two-membrane structure, negative membrane properties can additionally be modified.

Figure 14:
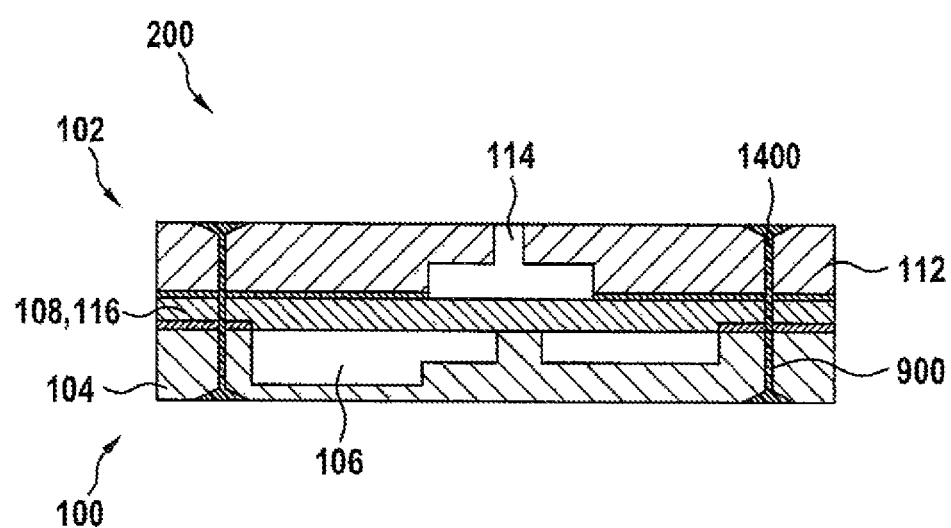
FIG. 14 shows a view of an analysis cartridge with rivets according to an illustrative embodiment of the present disclosure.

FIG. 14 shows a view of an analysis cartridge 200 with rivets 1400 according to an illustrative embodiment of the present disclosure. The analysis cartridge 200 corresponds to the analysis cartridge in FIG. 10. In contrast to the latter, the fluidic part 100 has through-bores 900, like the pneumatic part 102. The rivets 1400 are arranged in the through-bores 900 and extend from the rear face of the fluidic part 100 to the rear face of the pneumatic part 102, in order to mechanically prestress the analysis cartridge 200. The rivets 1400 are flush with the rear faces and each have a conical head at the end.

In one illustrative embodiment, the membranes 108, 116 are connected by laser welding and mechanical pressing.

In one illustrative embodiment, a sectional view of an LOC cartridge 200 constructed from four layers 104, 108, 112, 116 is shown. The pressing is effected by means of rivets (joining technique). A pneumatic duct is integrated in the pneumatic part 102.

The mechanical pressing can take place here at multiple discrete positions, wherein the microfluidic structures 106 are sealed off flat in a chip. In one embodiment, the layers have through-holes 900, as a result of which a join can be effected, for example, by rivets 1400, in particular plastic rivets. Alternatively, screws or similar connection methods can also be used.

Figure 15:
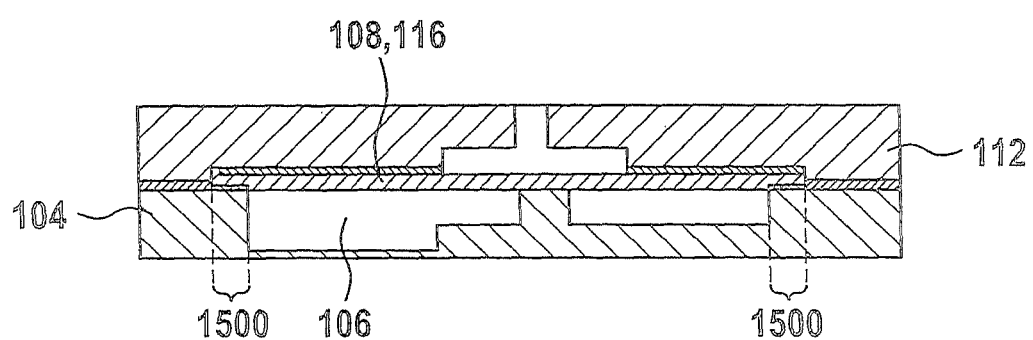
FIG. 15 shows a view of an analysis cartridge with sealing edge according to an illustrative embodiment of the present disclosure.

FIG. 15 shows a view of an analysis cartridge 200 with sealing edge 1500 according to an illustrative embodiment of the present disclosure. The analysis cartridge 200 corresponds to the view in FIG. 2. In contrast to FIG. 2, the membranes 108, 116 extend across the first substrate 104 and the second substrate 112 only over a partial surface area. At the sealing edge 1500, the membranes 108, 116 are clamped on both sides by the substrates 104, 112. Outside the area of the membranes 108, 116, the substrates 104, 112 are connected directly to each other.

In one illustrative embodiment, the joining of the surfaces takes place directly between the pneumatic 102 and fluidic layer 100, for example by thermal bonding, ultrasonic bonding or laser welding. The elastic membrane 108, 116 is structured in order to expose a bond face 1500 between pneumatic 102 and fluidic layer 100. Moreover, the elastic membrane 108, 116 is, by way of example, recessed into the pneumatic 102 and fluidic layer 100. The membrane 108, 116 protrudes above the fluidic network 106 and is clamped between pneumatic 102 and fluidic layer 100, as a result of which it functions as a "sealing ring".

In one embodiment, heterogeneous materials are used for bringing together the fluidic layer 104 with the multi-layer structure consisting of pneumatic substrate 112 and elastic membrane 108, 116. The joining is effected by mechanical pressing or connection of the fluidic substrate 104 to the elastic membrane 108 or the pneumatic layer 112 as a force-fit sealing structure. This is done by the fluidic layer 104 being brought together with the pneumatic layer 102 and the elastic membrane 108, these being pressed together, and this pressing being kept stable over the long term. The elastic membrane 108 serves here as sealing material for the structures 106 in the fluidic layer 104. Here, the elastic membrane 108 can be used as a surface seal, or it can be structured such that it overlaps the edge area 1500 of the fluidic structures 106 and thus seals off the fluidic structures 106 like a "sealing ring". The elastic membrane 108 here can be integrated completely between the pneumatic and fluidic layers 104, 112 or can be slightly recessed in one substrate 104, 112 or in both substrates. In the mechanical pressing, the elastic material can be compressed or squeezed. The pressing is so strong that no relevant gas or fluid leakage of the microfluidic structures 106 can arise.

In one embodiment, linear or planar pressing is also used in addition to discrete joining points. Thus, for example, the elastic membrane 108, 116 can be cut out and the two pneumatic and fluidic layers 104, 112 are joined by means of ultrasonic bonding. Here, the energy input typically takes place via energy acceptors that surround the fluidic structures 106. If the material combinations so permit, a bond can also be produced directly between fluidic and elastic membrane 108, 116. Moreover, adhesive joining methods are also possible, or joining methods with temperature coupling-in, such as thermal bonding, vibration bonding, thermal caulking or heated-tool welding. Depending on the embodiment, the bond can be made between the fluidic layer 104 and the elastic membrane 108 or between the fluidic layer 104 and the pneumatic layer 112. In the latter case, the elastic membrane 108, 116 is structured such that a contact is permitted between pneumatic and fluidic layers.

In one embodiment, the pneumatic and fluidic layer 104, 112 with cut-out and integrated elastomer membrane 108, 116 is also joined by laser welding. Here, discrete surfaces, contours, e.g. of the fluidic structures 106, or the entire contact face can be joined to each other.

Figure 16:
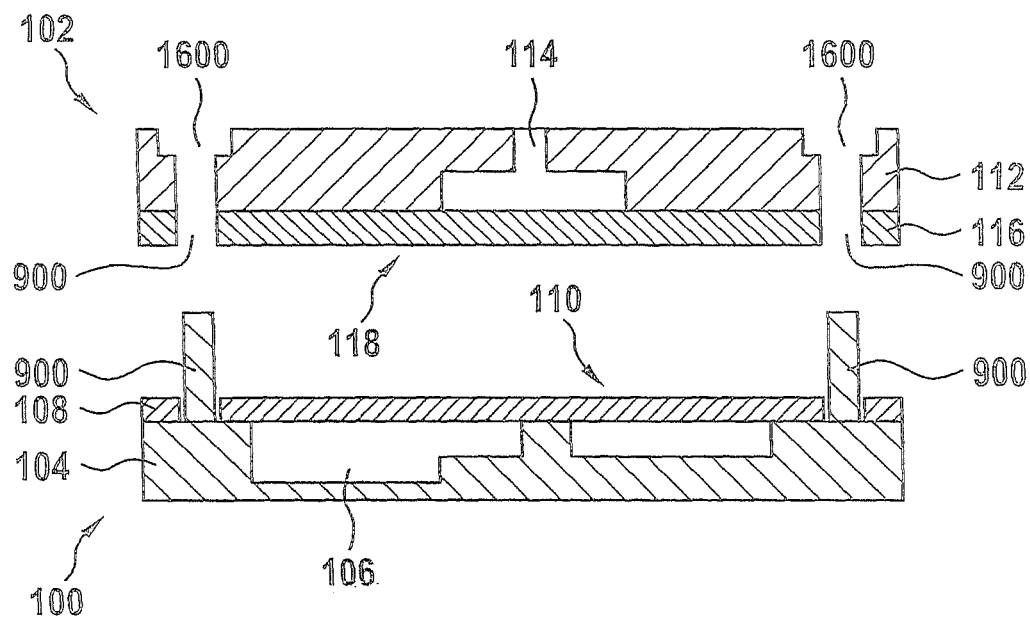
FIG. 16 shows a view of a fluidic part and of a pneumatic part with guide elements prior to alignment, according to an illustrative embodiment of the present disclosure.

FIG. 16 shows a view of a fluidic part 100 and of a pneumatic part 102 with connection elements 900 prior to alignment, according to an illustrative embodiment of the present disclosure. The fluidic part 100 and the pneumatic part 102 correspond to the view in FIG. 9. The fluidic part 100 has the first substrate 104 with the first structure 106 and the first membrane 108. The first membrane is arranged on the first joining face 110 and closes the first structure 106 in a fluid-tight manner. The first structure 106 can be designated as fluidic. The fluidic part 100 has, as connection elements 900, pins protruding above the first joining face 110 and the first membrane 108. The pneumatic part 102 has the second substrate 112 with the second structure 114 and the second membrane 116. The second membrane 116 is arranged on the second joining face 118 and closes the second structure 114. The second structure 114 can be designated as pneumatic or pneumatic duct. The pneumatic part 102 has, as connection elements 900, through-holes 900 that are arranged matching the pins 900. In addition, on the rear face opposite the second joining face 118, the pneumatic part 102 has recesses 1600, which are arranged concentrically with respect to the through-holes 900.

A carrier substrate 104, 112, which contains pneumatic or hydraulic ducts 106, 114, is selectively joined to a structured elastic membrane 108, 116 by laser welding. As substrates 104, 112 of the pneumatic layer 102, and also of the later fluidic layer 100, it is possible to use thermoplastics such as COP, COC, PC, PA, PU, PP, PE, PET or PMMA. As elastic membrane 108, 116, it is possible to use elastomers or thermoplastic elastomers, such as olefin-based thermoplastic elastomers, cross-linked olefin-based thermoplastic elastomers, urethane-based thermoplastic elastomers, thermoplastic polyester elastomers, thermoplastic copolyesters, styrene-based thermoplastic elastomers, thermoplastic copolyamides, polyether-based thermoplastic elastomers, polyethylene-based thermoplastic elastomers or TPS, such as styrene block copolymers or styrene block polymers, optionally with ethylene-butylene. Combinations with further materials are also possible. Alternatively or in addition, it is also possible to use elastic multi-layer films or composite films with a laser-weldable surface facing the pneumatic substrate. A further alternative concerns plastically deformable monofilms made from the abovementioned thermoplastic materials. In one illustrative embodiment, the elastic membranes 108, 116 are structured by means of punching or laser ablation. Thereafter, the pneumatic layer 102 or the fluidic layer 102 and the elastic membrane 116 or 108 are subjected to pressure (p<3 bar; F<5 kN) and joined by means of laser welding. Lasers in the IR range are typically used, particularly at wavelengths of 1064 nm. Here, either the pneumatic substrate 112 or the elastic membrane 116, or both, will act as absorber for the laser-induced energy. The laser energy is coupled onto the interface of the two layers by the material transparent for the wavelength of the laser light. Alternatively, the laser light can also be coupled onto the rear face of an absorber, wherein the heat is transmitted onward to the interface of the materials in order to achieve welding. The welding here takes place selectively on defined surfaces or selectively on defined weld paths, such that, after the joining process, surfaces are present where the elastic membrane 108, 116 and the pneumatic substrate 112 or the fluidic substrate 102 are not connected to each other.

Figure 17:
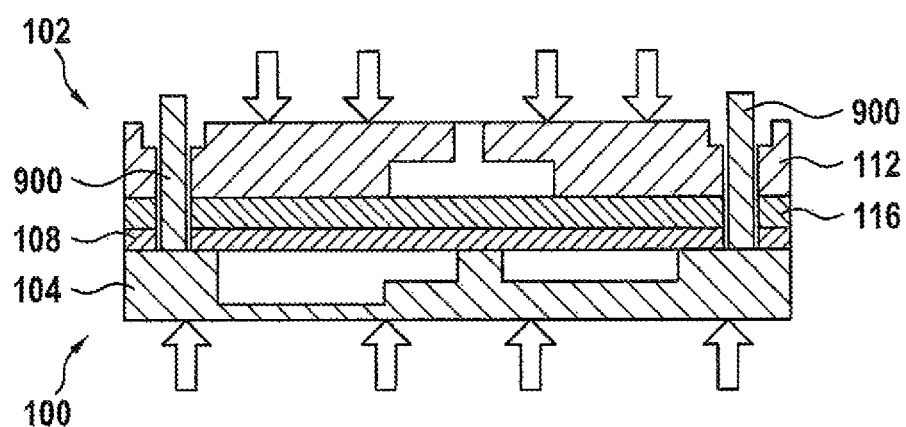
FIG. 17 shows a view of a fluidic part and of a pneumatic part with guide elements during alignment, according to an illustrative embodiment of the present disclosure.

FIG. 17 shows a view of a fluidic part 100 and of a pneumatic part 102 with guide elements 900 during alignment, according to an illustrative embodiment of the present disclosure. The fluidic part 100 and the pneumatic part 102 correspond to the view in FIG. 16. The pins 900 are arranged in the through-holes 900, and the first membrane 108 bears on the second membrane 116. By means of the pins 900 in the holes 900, the fluidic part 100 and the pneumatic part 102 are aligned on each other and are held in a predefined position relative to each other. During the alignment, pressure is applied to the rear face of the fluidic part 100 and to the rear face of the pneumatic part 102 in order to press the membranes 108, 116 onto each other. The membranes 108, 116 can be connected to each other. The pins 900 pass through the through-holes 900 and protrude from the rear face of the pneumatic part 102.

Figure 18:
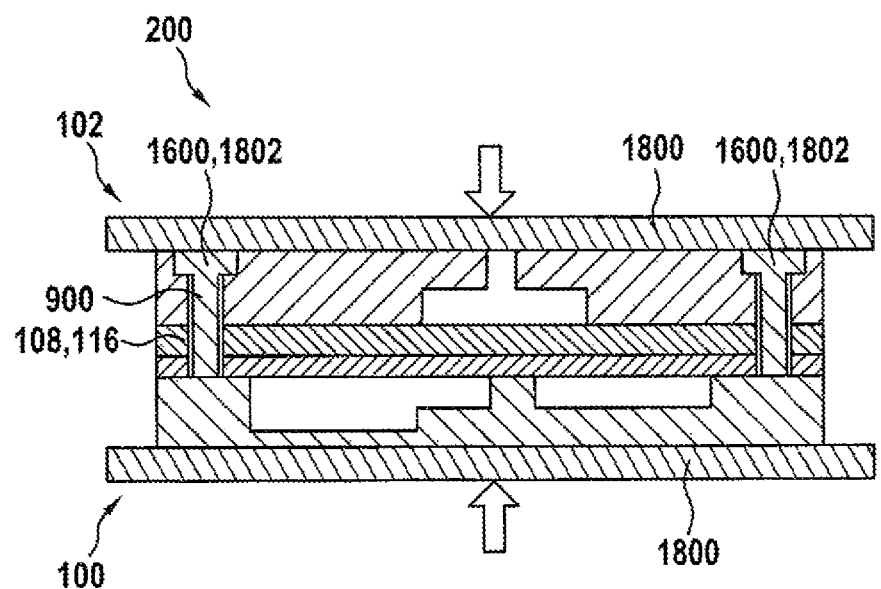
FIG. 18 shows a view of a fluidic part and of a pneumatic part with guide elements during connection, according to an illustrative embodiment of the present disclosure.

FIG. 18 shows a view of a fluidic part 100 and of a pneumatic part 102 with guide elements 900 during connection, according to an illustrative embodiment of the present disclosure. The fluidic part 100 and the pneumatic part 102 are aligned on each other as in FIG. 17, and the first membrane 108 bears on the second membrane 116. Pressure plates 1800 of a connection device bear with pressure on the rear faces of the fluidic part 100 and of the pneumatic part 102. At least the pressure plate 1800 bearing on the pneumatic part 102 is heated. By the temperature of the pressure plate 1800, the parts of the pins 900 protruding above the rear face are melted and are reshaped into the recesses 1600 by the pressure. The pins 900 are now flattened and have disk-like prolongations 1802 which latch into the recesses 1600. By means of the prolongations, the fluidic part 100 is fixedly connected to the pneumatic part 102 to form the analysis cartridge 200.

FIGS. 16 to 18 show an illustrative embodiment of a joining process by means of integrated joining pins 900. The joining pins 900 can be realized in the production process (e.g. injection molding) of the associated layer 100. The further layers 102, 108, 116 have corresponding through-holes 900. The layers 100, 102, 108, 116 are pressed against each other under pressure. The pressing can be carried out under vacuum. The joining pins 900 are melted and pressed into special recesses 1600 of the holding layer 102, such that the surface has no elevation. The joining disks 1800 in the joining bay 1600 maintain the mechanical pressure applied during production, such that sealed-off fluidic networks 106 are obtained. Depending on the process, the alignment and connection can also be carried out in one step.

In other words, FIGS. 16, 17 and 18 show an illustrative embodiment of mechanical joining of multi-layer LOC cartridges 200 with elastomeric sealing films 108, 116.

Joining methods at elevated temperature can also be used. Thus, for example, pins 900 perpendicular to the plane can be obtained directly in injection molding of a pneumatic and/or fluidic layer 104, 112. The elastic membrane 108, 116, like the mating piece of the pneumatic layer or fluidic layer, has through-holes 900. The layers are pressed together, as a result of which the pins 900 protrude from the mating piece. These pins are then heated thermally (above the glass transition temperature of the material), such that the material can flow and thus deforms when a force is applied, with the result that permanent pressing is obtained. Typically, the connections are introduced such that the outer surfaces of the structure 200 are planar and have no elevations. For this purpose, the mating piece typically has a depression 1600. The bonding forces can be varied via the contact pressure/force or path-controlled process controls.

In a further embodiment, the joining pins 900 are designed such that they act as dowel pins in the mating substrate and, during the joining process, the layers are aligned with each other and adjusted. An alternative is that only a partial area of the guide pin 900 is designed as a dowel pin (e.g. the lower part), and another part (the upper part) is flexible, e.g. in order to simplify "threading" of the substrates.

Figure 19:
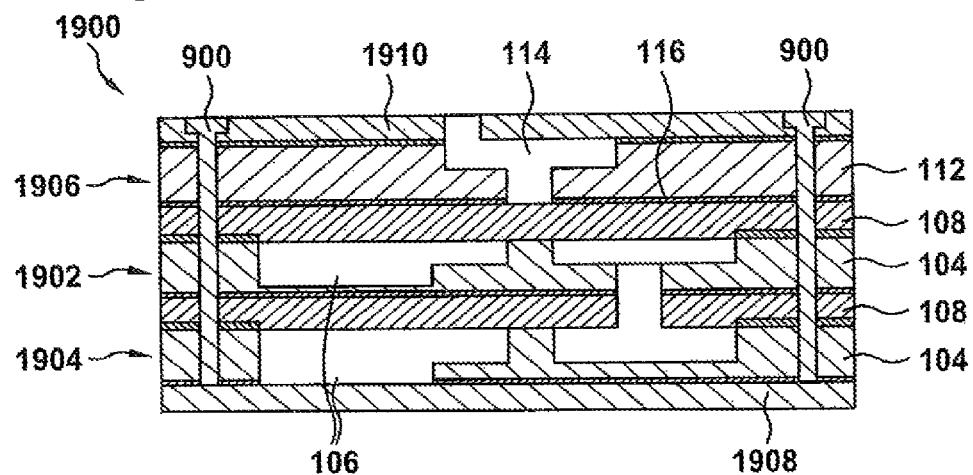
FIG. 19 shows a view of an analysis cartridge with a first fluidic part and a second fluidic part according to an illustrative embodiment of the present disclosure.

FIG. 19 shows a view of an analysis cartridge 1900 with a first fluidic part 1902 and a second fluidic part 1904 according to an illustrative embodiment of the present disclosure. The analysis cartridge 1900 also has a pneumatic part 1906. The fluidic parts 1902, 1904 are of similar design. Each of the fluidic parts 1902, 1904 has, like the fluidic part in FIGS. 1 to 18, a first substrate 104 and a first membrane 108. Like the pneumatic part in FIGS. 1 to 18, the pneumatic part 1906 has a second substrate 112 and a second membrane 116. The first fluidic part 1902 is arranged on the second fluidic part 1904. The pneumatic part 1906 is arranged on the first fluidic part 1902. The fluidic parts 1902, 1904 and the pneumatic part 1906 form a stack. The stack has a terminating base plate 1908 and a terminating cover plate 1910. The first membrane of the second fluidic part 1904 has an opening. Fluid ducts 106 in the fluidic parts 1902, 1904 are fluidically connected via the opening in the first membrane 108. The pneumatic part 1906 has pneumatic ducts 114. The pneumatic ducts 114 are separated from the fluid ducts 106 by the first and second membrane 108, 116. As in FIG. 18, the stack is connected by connection elements 900. The connection elements 900 connect the base plate 1908 and the cover plate 1910 mechanically to each other and align the fluidic parts 1902, 1904 and the pneumatic part 1906 to each other. The connection elements 900 pass through the fluidic parts 1902, 1904 and the pneumatic part 1906.

In one illustrative embodiment, the analysis cartridge 1900 is a multi-layer structure in which several layers 1902, 1904, 1906 are joined by mechanical pressing or are connected via several laser-welding planes. A layer here can be sealed off by a combination of laser welding and mechanical pressing or in each case only by one of the joining methods. For the mechanical pressing, any desired joining methods (e.g. also adhesive methods) can be used.

In a further embodiment, further layers are periodically applied, by further mechanical pressing or laser-welding processes, in order to produce multi-layer systems with more than four layers. Moreover, seals can also be applied to the four-layer stack 200 in order to cover any ducts lying on the outside. Any other desired joining methods can also be used for this purpose.

Figure 20:
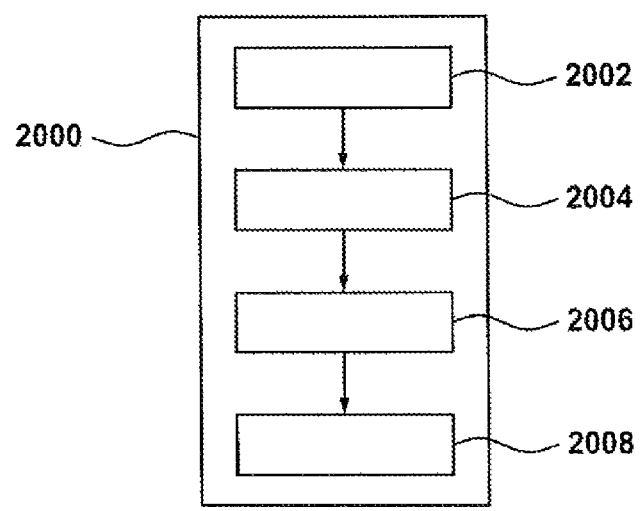
FIG. 20 shows a block diagram of a device for producing an analysis cartridge according to an illustrative embodiment of the present disclosure.

FIG. 20 shows a block diagram of a device 2000 for producing a pneumatically actuatable microfluidic analysis cartridge, according to an illustrative embodiment of the present disclosure. The device has a means 2002 for provision, a means 2004 for closure, a means 2006 for alignment, and a means 2008 for connection. The means 2002 for provision is designed to provide a fluidic part of the analysis cartridge and a pneumatic part of the analysis cartridge. The fluidic part is designed to perform fluidic basic operations of a biochemical analysis process. The pneumatic part is designed to control the basic operations using compressed air. The means 2004 for closure is designed to close a joining side of the fluidic part with a first fluid-tight elastic membrane. Moreover, the means 2004 for closure is designed to close a joining side of the pneumatic part with a second membrane. The means 2006 for alignment is designed to align the first membrane on the second membrane. The means 2008 is designed to connect the fluidic part and the pneumatic part, in order to obtain the analysis cartridge.

The illustrative embodiments that have been described and that are shown in the figures are chosen only as examples. Different illustrative embodiments can be combined in full or in respect of individual features. An illustrative embodiment can also be supplemented by features of another illustrative embodiment. Moreover, method steps according to the disclosure can be repeated and can be carried out in a sequence other than that described. Where an illustrative embodiment includes an "and/or" link between a first feature and a second feature, this should be understood as meaning that the illustrative embodiment has both the first feature and also the second feature in a first configuration, and has either only the first feature or only the second feature in a further configuration.

What is claimed is:

1. A method of producing a pneumatically actuated microfluidic analysis cartridge, comprising:
    closing a joining side of a fluidic part of the analysis cartridge with a first fluid-tight elastic membrane, the fluidic part configured such that fluidic basic operations of a biochemical analysis process are performed in the fluidic part;
    closing a joining side of a pneumatic part of the analysis cartridge with a second membrane, the pneumatic part configured such that pneumatic actuation of the cartridge controls the basic operations using air pressure in the pneumatic part;
    aligning the closed joining side of the fluidic part with respect to the closed joining side of the pneumatic part; and
    connecting the aligned fluidic part and the aligned pneumatic part to form the analysis cartridge,
    wherein, after connecting of the aligned fluidic part and the aligned pneumatic part, the first elastic membrane is configured to seal against a first portion of the fluidic part so as to disable fluid flow through the fluidic part, and the first and second elastic membranes are configured to jointly elastically deform such that the first elastic membrane separates from the first portion of the fluidic part to enable fluid flow through the fluidic part.

2. The method according to claim 1, wherein the closing steps include at least one of:
    the closing of the joining side of the fluidic part including connecting the joining side of the fluidic part with the first fluid-tight elastic membrane using laser energy directed onto the joining side of the fluidic part; and
    the closing of the joining side of the pneumatic part including connecting the joining side of the pneumatic part with the second membrane using laser energy directed onto the joining side of the pneumatic part.

3. The method according to claim 1, wherein the connecting includes cohesively connecting the first fluid-tight elastic membrane and the second membrane to each other over at least a partial surface area.

4. The method according to claim 1, wherein the connecting includes mechanically pressing the fluidic part and the pneumatic part into each other.

5. The method according to claim 1, wherein the closing of the joining side of the fluidic part includes coating the first fluid-tight elastic membrane over at least a partial surface area such that at least one of diffusion properties and permeation properties of the first fluid-tight elastic membrane are modified.

6. The method according to claim 1, wherein:
    the aligning includes positioning a third elastic membrane between the first fluid-tight elastic membrane and the second membrane, and
    the connecting includes connecting the first and second elastic membranes to opposite sides of the third elastic membrane.

7. The method according to claim 1, wherein:
    the fluidic part includes a sealing element which protrudes from the joining side of the fluidic part, and
    the connecting includes pressing the sealing element of the fluidic part into the second membrane such that the fluidic part and the pneumatic part are connected in a fluid-tight manner.

8. The method according to claim 1, wherein:
    the fluidic part and the pneumatic part each respectively include at least two guide elements; and
    the aligning includes aligning the fluidic part and the pneumatic part using at least one of the at least two guide elements of the fluidic part and the at least two guide elements of the pneumatic part.

9. The method according to claim 8, wherein:
    the closing of the joining side of the fluidic part includes aligning the first fluid-tight elastic membrane on the at least two guide elements of the fluidic part; and
    the closing of the joining side of the pneumatic part includes aligning the second membrane on the at least two guide elements of the pneumatic part.

10. The method according to claim 1, wherein the connecting includes pressurizing at least one of the fluidic part and the pneumatic part so as to connect the first fluid-tight membrane to the second membrane using pressure in the at least one of the fluidic part and the pneumatic part.

11. A pneumatically actuated microfluidic analysis cartridge comprising:
    a fluidic part in which fluidic basic operations of a biochemical analysis process are performed;
    a pneumatic part configured such that pneumatic actuation of the cartridge controls the basic operations using air pressure in the pneumatic part; and
    a first fluid-tight elastic membrane configured to close the joining side of the fluidic part; and
    a second fluid-tight elastic membrane configured to close the joining side of the pneumatic part, the first elastic membrane and the second elastic membrane are connected to each other and positioned between the fluidic part and the pneumatic part,
    wherein the first elastic membrane is configured to seal against a first portion of the fluidic part so as to disable fluid flow through the fluidic part, and the first and second elastic membranes are configured to jointly elastically deform such that the first elastic membrane separates from the first portion of the fluidic part to enable fluid flow through the fluidic part.

12. The analysis cartridge according to claim 11, wherein the joining side of the fluidic part and the joining side of the pneumatic part comprise different materials.

13. The analysis cartridge according to claim 11, wherein:
    the first elastic membrane is transparent for laser light in a first wavelength range,
    the second elastic membrane is transparent for laser light in a second wavelength range,
    the first wavelength range is different from the second wavelength range, and
    the first and second elastic membranes are connected to one another.

14. The analysis cartridge according to claim 11, further comprising:
an adhesive layer bonding the first elastic membrane and the second elastic membrane together.

15. The analysis cartridge according to claim 11, further comprising:
a metal layer coating one of the first elastic membrane and the second elastic membrane on a side of the one of the first membrane and the second membrane facing the other of the first membrane and the second membrane.

16. The analysis cartridge according to claim 11, further comprising:
a connection element extending through the first and second elastic membranes from one of the fluidic part and the pneumatic part into the other of the fluidic part and the pneumatic part and configured to clamp the fluidic part and the pneumatic part together.

17. The analysis cartridge according to claim 16, wherein:
the fluidic part defines a first through-bore,
the pneumatic part defines a second through-bore, and
the connection element includes a rivet extending through the first through-bore and the second through bore, the rivet including a first end having a first widened portion and a second end having a second widened portion.

18. A method of producing a pneumatically actuated microfluidic analysis cartridge, comprising:
closing a joining side of a fluidic part of the analysis cartridge with a first fluid-tight elastic membrane;
closing a joining side of a pneumatic part with a second fluid-tight elastic membrane, the pneumatic part being configured such that pneumatic actuation of the analysis cartridge controls fluidic basic operations of a biochemical analysis process in the fluidic part using air pressure in the pneumatic part;
aligning the joining side of the fluidic part with respect to the joining side of the pneumatic part after the closing of the one of the joining side of the fluidic part and the joining side of the pneumatic part in such a way that the first and second fluid-tight elastic membranes are interposed between the fluidic part and the pneumatic part; and
connecting the aligned fluidic part and the pneumatic part to form the analysis cartridge by:
passing a connecting element from one of the fluidic part and the pneumatic part through a first through-hole defined in the first elastic membrane, through a second through-hole defined in the second elastic membrane, and through a third through-hole defined in the other of the fluidic part and the pneumatic part; and
fixing the connecting element to the other of the fluidic part and the pneumatic part at a side of the other of the fluidic part and the pneumatic part opposite the one of the fluidic part and the pneumatic part,
wherein, after connecting of the aligned fluidic part and the aligned pneumatic part, the first elastic membrane is configured to seal against a first portion of the fluidic part so as to disable fluid flow through the fluidic part, and the first and second elastic membranes are configured to jointly elastically deform such that the first elastic membrane separates from the first portion of the fluidic part to enable fluid flow through the fluidic part.

19. The method of claim 18, wherein the fixing of the connecting element further comprises compressing the pneumatic part and the fluidic part together with pressure plates thereby compressing a first end portion of the connecting element, which extends beyond the side of the other of the fluidic part and the pneumatic part opposite the one of the fluidic part and the pneumatic part, and forming a flattened end portion at the first end portion fixedly connecting the fluidic part and the pneumatic part to one another.

20. The method according to claim 1, wherein:
the connecting of the aligned fluidic part and the aligned pneumatic part includes connecting the pneumatic part to the fluidic part in such a way that a chamber defined in the pneumatic part is arranged opposite the first portion of the fluidic part;
the cartridge is configured with a first actuation state in which the air pressure in the pneumatic part causes the first elastic membrane to seal against the first portion so as to disable fluid flow through the fluidic part; and
the cartridge is configured with a second actuation state in which the air pressure in the pneumatic part causes the first and second elastic membranes to elastically deform into the chamber so as to separate the first elastic membrane from the first portion and enable fluid flow through the fluidic part.

21. The analysis cartridge according to claim 11, wherein:
the pneumatic part defines a chamber arranged opposite the first portion of the fluidic part;
the cartridge has a first actuation state in which the air pressure in the pneumatic part causes the first elastic membrane to seal against the first portion so as to disable fluid flow through the fluidic part; and
the cartridge has a second actuation state in which the air pressure in the pneumatic part causes the first and second elastic membranes to elastically deform into the chamber so as to separate the first elastic membrane from the first portion and enable fluid flow through the fluidic part.

* * * * *